(12) United States Patent
Brummer et al.

(10) Patent No.: US 9,611,195 B2
(45) Date of Patent: Apr. 4, 2017

(54) FLEXIBLE BUTADIENE EXTRACTION PROCESS

(71) Applicant: Lummus Technology Inc., Bloomfield, NJ (US)

(72) Inventors: Robert J. Brummer, Wharton, NJ (US); Thomas Alexander Dwyer, Wayne, NJ (US)

(73) Assignee: Lummus Technology Inc., Bloomfield, NJ (US)

( * ) Notice: Subject to any disclaimer, the term of this patent is extended or adjusted under 35 U.S.C. 154(b) by 351 days.

(21) Appl. No.: 14/034,806

(22) Filed: Sep. 24, 2013

(65) Prior Publication Data

US 2014/0100405 A1    Apr. 10, 2014

Related U.S. Application Data

(60) Provisional application No. 61/711,540, filed on Oct. 9, 2012.

(51) Int. Cl.
| | |
|---|---|
| *B01D 3/40* | (2006.01) |
| *C07C 7/04* | (2006.01) |
| *C07C 7/08* | (2006.01) |
| *B01D 3/14* | (2006.01) |

(52) U.S. Cl.
CPC ............... *C07C 7/04* (2013.01); *B01D 3/141* (2013.01); *B01D 3/143* (2013.01); *B01D 3/40* (2013.01); *C07C 7/08* (2013.01)

(58) Field of Classification Search
None
See application file for complete search history.

(56) References Cited

U.S. PATENT DOCUMENTS

| | | |
|---|---|---|
| 4,162,198 A | 7/1979 | Stockburger et al. |
| 4,310,388 A | 1/1982 | Volkamer et al. |
| 5,242,550 A | 9/1993 | Asselineau et al. |
| 6,337,429 B1 | 1/2002 | Kindler et al. |
| 7,132,038 B2 | 11/2006 | Bohner et al. |
| 7,226,527 B2 | 6/2007 | Bohner et al. |
| 7,393,992 B2 | 7/2008 | Hill et al. |
| 7,432,411 B2 | 10/2008 | Adrian et al. |
| 7,482,500 B2 | 1/2009 | Johann et al. |
| 7,619,126 B2 | 11/2009 | Heida |
| 7,692,053 B2 | 4/2010 | Heida |

FOREIGN PATENT DOCUMENTS

| | | |
|---|---|---|
| CN | 1298375 A | 6/2001 |
| CN | 1918090 A | 2/2007 |

OTHER PUBLICATIONS

International Search Report and Written Opinion mailed Jan. 23, 2014 in corresponding International Appilcation No. PCT/US2013/060519 (12 pages).
Search Report and Written Opinion issued Apr. 21, 2016 in corresponding Singapore application No. 11201503175X (11 pages).
Office Action issued Apr. 1, 2016 in corresponding Canadian application No. 2,887,299 (5 pages).
First Office Action issued Feb. 22, 2016 in corresponding Chinese application No. 201380057858.5 (w/translation) (18 pages).
Extended European Search Report issued May 2, 2016 in corresponding European application No. 13845575.3 (6 pages).

*Primary Examiner* — Tam M Nguyen
(74) *Attorney, Agent, or Firm* — Osha Liang LLP

(57) ABSTRACT

A butadiene extraction processes designed for flexible operations, with or without a compressor, is disclosed. The ability to run at both high and low pressures provides added process flexibility.

10 Claims, 1 Drawing Sheet

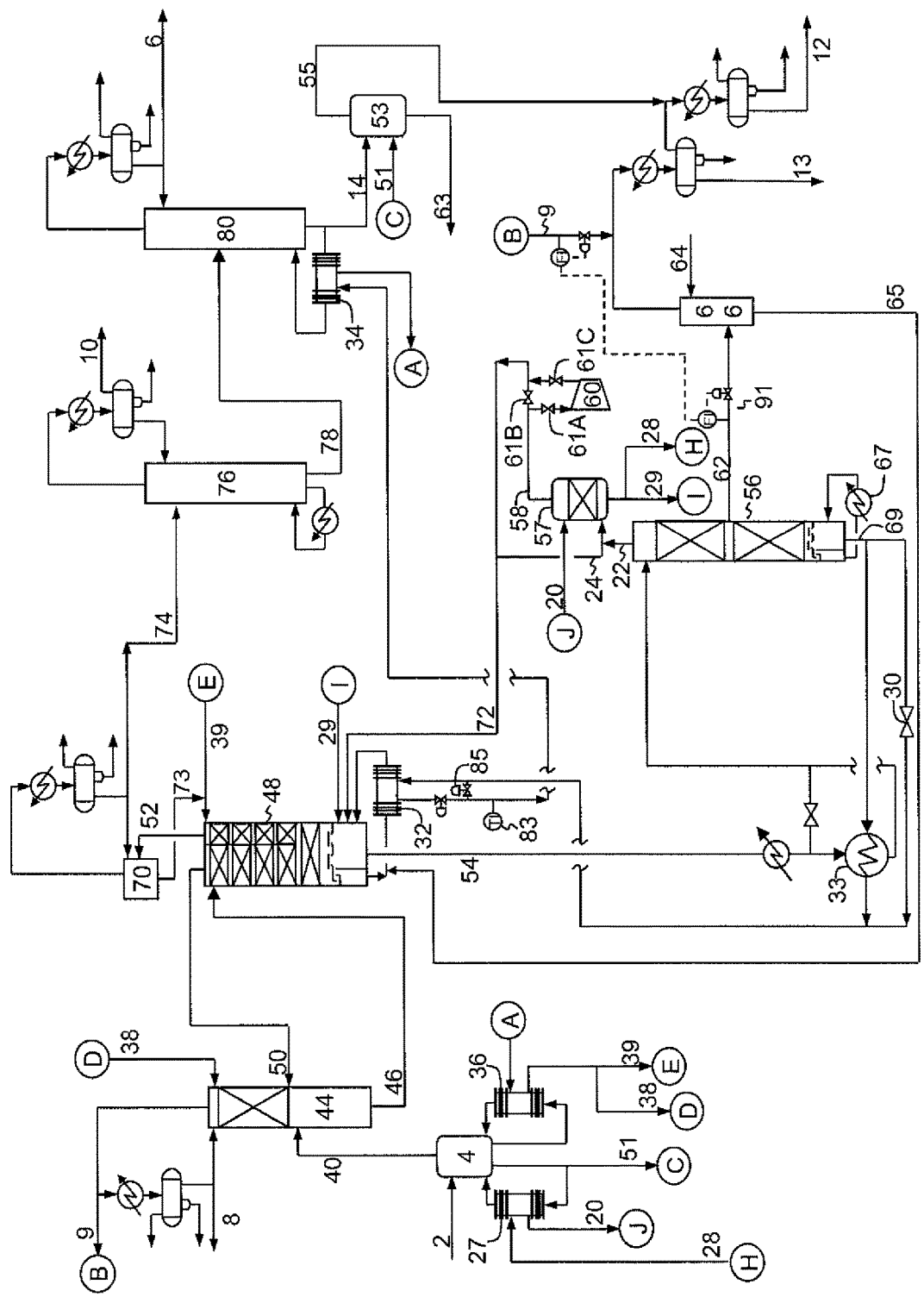

FLEXIBLE BUTADIENE EXTRACTION PROCESS

CROSS-REFERENCE TO RELATED APPLICATIONS

This application, pursuant to 35 U.S.C. §119(e), claims priority to U.S. Provisional Application Ser. No. 61/711,540, filed Oct. 9, 2012, which is herein incorporated by reference in its entirety.

FIELD OF THE DISCLOSURE

Embodiments disclosed here relate to recovery of butadiene from a mixed hydrocarbon stream. More specifically, embodiments disclosed herein relate to an improved butadiene extraction process capable of operating at high or low pressure conditions.

BACKGROUND

Butadiene is an important base chemical and is used, for example, to prepare synthetic rubbers (butadiene homopolymers, styrene-butadiene-rubber or nitrile rubber) or for preparing thermoplastic terpolymers (acrylonitrile-butadiene-styrene copolymers). Butadiene is also converted to sulfolane, chloroprene and 1,4-hexamethylenediamine (via 1,4-dichlorobutene and adiponitrile). Dimerization of butadiene also allows vinylcyclohexene to be generated, which can be dehydrogenated to form styrene.

Butadiene can be prepared from saturated hydrocarbons by refining process or by thermal cracking (steam cracking) processes, in which case naphtha is typically used as the raw material. In the course of refining or steam cracking of naphtha, a mixture of methane, ethane, ethene, acetylene, propane, propene, propyne, allene, butenes, butadiene, butynes, methylallene, $C_4$ and higher hydrocarbons are obtained.

Owing to the small differences in the relative volatilities of the components of a $C_4$ cut, obtaining 1,3-butadiene from the $C_4$ cut is a complicated distillation problem. Therefore, the separation is carried out by extractive distillation, i.e., a distillation with addition of an extractant which has a higher boiling point than the mixture to be separated and which increases the differences in the relative volatilities of the components to be separated. The use of suitable extractants allows a crude 1,3-butadiene fraction to be obtained from the $C_4$ cut mentioned by means of extractive distillation, and said fraction is subsequently further purified in purifying distillation columns.

Butadiene recovery processes typically use 3- or 4-column extractive distillation systems to separate a mixed $C_4$ stream into product fractions, including a lights/butane/butenes stream (Raffinate-1 product), a crude butadiene product, which may be sent to a conventional distillation system for further purification, and $C_3$ acetylenes (propyne) and $C_4$ acetylenes streams, which may be sent to a selective hydrogenation unit, for example.

In the present context, crude 1,3-butadiene refers to a hydrocarbon mixture which has been obtained from a $C_4$ cut from which at least 90% by weight of the sum of butanes and butenes, preferably at least 98% by weight of the sum of butanes and butenes, more preferably at least 99% by weight of the sum of butanes and butenes, and simultaneously at least 90% by weight of the $C_4$ acetylenes, preferably at least 96% by weight of the $C_4$ acetylenes, more preferably at least 99% by weight of the $C_4$ acetylenes, has been removed.

Crude 1,3-butadiene contains the 1,3-butadiene product of value frequently in a proportion of at least 80% by weight, preferably 90% by weight, more preferably more than 95% by weight, remainder impurities. Accordingly, pure 1,3-butadiene refers to a hydrocarbon mixture which contains the 1,3-butadiene product of value in a proportion of at least 98% by weight, preferably of at least 99.5% by weight, more preferably in the range between 99.7 and 99.9% by weight, remainder impurities.

Typical processes to recover butadiene from mixed $C_4$ streams include extractive distillation processes, which may incorporate use of selective solvents. Examples of extractive distillation processes are found, for example, in U.S. Pat. Nos. 7,692,053, 7,393,992, 7,482,500, 7,226,527, 4,310,388, and 7,132,038, among others.

The extractive distillation processes described in the above mentioned patents typically fall into one of two categories, a conventional low pressure process including a compressor or a high pressure "compressorless" process, such as disclosed in U.S. Pat. No. 7,692,053.

Various equipment specifications (design criteria) are different in the "conventional" low pressure design as compared to the "compressorless" high pressure process. For example, for the compressorless design, the degasser may be operated at an overhead pressure of about 4.21 kg/cm² gage, slightly above the extractive distillation system (including the main washer, rectifier and afterwasher) pressure. Consequently, the degasser operates at correspondingly higher temperatures: about 148° C. at the top of the degasser and about 193° C. at the bottom of the degasser. In contrast, the degasser in the conventional design may be operated at an overhead pressure of only 0.7 kg/cm² gage, and at much lower temperatures: about 105° C. at the top of the degasser and about 149° C. at the bottom of the degasser. Additionally, solvent heat recovery schemes are different between the two designs to achieve respective process efficiencies at the disparate pressures.

SUMMARY OF THE CLAIMED EMBODIMENTS

It has now been found that butadiene extraction processes may be designed for flexible operations, with or without a compressor, while adding little additional capital investment cost. The ability to run at both high and low pressures provides added process flexibility.

In one aspect, embodiments disclosed herein relate to a system for recovering 1,3-butadiene from a $C_4$ fraction in both a high pressure mode or a low pressure mode. The system may include, among other components: a feed vaporization system for at least partially vaporizing a hydrocarbon feed containing butanes, butenes, 1,2-butadiene, 1,3-butadiene, $C_4$ acetylenes, $C_3$ acetylenes, and $C_{5+}$ hydrocarbons; an extractive distillation system for contacting the vaporized hydrocarbon fraction with a solvent to selectively dissolve a portion of the hydrocarbon fraction forming (a) an enriched solvent fraction comprising the 1,3-butadiene, the 1,2-butadiene, $C_4$ acetylenes, $C_3$ acetylenes, $C_{5+}$ hydrocarbons, and a first portion of the butanes and the butenes and (b) a vapor fraction comprising a second portion of the butanes and the butenes; a rectifier and afterwasher for at least partially degassing the enriched solvent and recovering a first vapor fraction comprising the first portion of the butanes and butenes, a second vapor fraction comprising the $C_3$ and $C_4$ acetylenes, 1,3-butadiene, 1,2-butadiene, and $C_{5+}$ hydrocarbons, and a bottoms fraction comprising partially degassed solvent; a degasser and cooling column for further degassing the solvent and recovering a liquid fraction comprising degassed solvent, a third vapor fraction comprising at least one of C4 acetylenes and 1,2-butadiene, and a fraction comprising C4 acetylenes. The system for recovering 1,3-butadiene is configured to operate alternatively (a) with the degasser in a high pressure mode, or (b) with the degasser in a low pressure mode.

In another aspect, embodiments disclosed herein relate to a system for recovering 1,3-butadiene from a $C_4$ fraction in both a high pressure mode or a low pressure mode. The system may include: a feed vaporization system for at least partially vaporizing a hydrocarbon feed containing butanes, butenes, 1,2-butadiene, 1,3-butadiene, $C_4$ acetylenes, $C_3$ acetylenes, and $C_{5+}$ hydrocarbons; an extractive distillation system for contacting the vaporized hydrocarbon fraction with a solvent to selectively dissolve a portion of the hydrocarbon fraction forming (a) an enriched solvent fraction comprising the 1,3-butadiene, the 1,2-butadiene, $C_4$ acetylenes, $C_3$ acetylenes, $C_{5+}$ hydrocarbons, and a first portion of the butanes and the butenes and (b) a vapor fraction comprising a second portion of the butanes and the butenes; a rectifier and afterwasher for at least partially degassing the enriched solvent and recovering a first vapor fraction comprising the first portion of the butanes and butenes, a second vapor fraction comprising the $C_3$ and $C_4$ acetylenes, 1,3-butadiene, 1,2-butadiene, and $C_{5+}$ hydrocarbons, and a bottoms fraction comprising partially degassed solvent; a degasser and cooling column for further degassing the solvent and recovering a liquid fraction comprising degassed solvent, a third vapor fraction comprising at least one of C4 acetylenes and 1,2-butadiene, and a fraction comprising C4 acetylenes; a compressor for compressing the third vapor fraction when operating in the low pressure mode; and a heat exchanger for indirectly heating the partially degassed solvent with the liquid fraction comprising degassed solvent when operating in the low pressure mode.

In another aspect, embodiments disclosed herein relate to a system for recovering 1,3-butadiene from a $C_4$ fraction in a high pressure mode or a low pressure mode. The system may include: a feed vaporization system for at least partially vaporizing a hydrocarbon feed containing butanes, butenes, 1,2-butadiene, 1,3-butadiene, $C_4$ acetylenes, $C_3$ acetylenes, and $C_{5+}$ hydrocarbons; an extractive distillation system for contacting the vaporized hydrocarbon fraction with a solvent to selectively dissolve a portion of the hydrocarbon fraction forming (a) an enriched solvent fraction comprising the 1,3-butadiene, the 1,2-butadiene, $C_4$ acetylenes, $C_3$ acetylenes, $C_{5+}$ hydrocarbons, and a first portion of the butanes and the butenes and (b) a vapor fraction comprising a second portion of the butanes and the butenes; a rectifier and afterwasher for at least partially degassing the enriched solvent and recovering a first vapor fraction comprising the first portion of the butanes and butenes, a second vapor fraction comprising the $C_3$ and $C_4$ acetylenes, 1,3-butadiene, 1,2-butadiene, and $C_{5+}$ hydrocarbons, and a bottoms fraction comprising partially degassed solvent; a degasser and cooling column for further degassing the solvent and recovering a liquid fraction comprising degassed solvent, a third vapor fraction comprising at least one of C4 acetylenes and 1,2-butadiene, and a fraction comprising C4 acetylenes. The system for recovering 1,3-butadiene is configured such that the cooling column is in operation during both the high pressure mode and the low pressure mode.

In another aspect, embodiments disclosed herein relate to a process for recovering 1,3-butadiene from a $C_4$ fraction, alternately, in a high pressure mode and a low pressure mode. The system may include: at least partially vaporizing a hydrocarbon feed containing butanes, butenes, 1,2-butadiene, 1,3-butadiene, $C_4$ acetylenes, $C_3$ acetylenes, and $C_{5+}$ hydrocarbons in a feed vaporization system; selectively dissolving a portion of the hydrocarbon fraction in an extractive distillation system by contacting the vaporized hydrocarbon fraction with a solvent, forming (a) an enriched solvent fraction comprising the 1,3-butadiene, the 1,2-butadiene, $C_4$ acetylenes, $C_3$ acetylenes, $C_{5+}$ hydrocarbons, and a first portion of the butanes and the butenes and (b) a vapor fraction comprising a second portion of the butanes and the butenes; at least partially degassing the enriched solvent in a rectifier and afterwasher and recovering a first vapor fraction comprising the first portion of the butanes and butenes, a second vapor fraction comprising the $C_3$ and $C_4$ acetylenes, 1,3-butadiene, 1,2-butadiene, and $C_{5+}$ hydrocarbons, and a bottoms fraction comprising partially degassed solvent; further degassing the solvent in a degasser and a cooling column and recovering a liquid fraction comprising degassed solvent, a third vapor fraction comprising at least one of C4 acetylenes and 1,2-butadiene, and a fraction comprising C4 acetylenes; alternatively (a) operating the degasser in a high pressure mode, and (b) operating the degasser in a low pressure mode.

Previous designs would have required many more changes to the processing scheme, resulting in either more investment cost or a less efficient process. By retaining much of the equipment used in the conventional process, and using this equipment when operating in compressorless mode, butadiene extraction processes according to embodiments disclosed herein are flexible and do not require re-optimization of the solvent heat recovery system. With respect to additional capital expenses, only one additional heat exchanger is required, along with minor changes to controls and equipment design conditions to allow operation at both high and low pressures.

Other aspects and advantages will be apparent from the following description and the appended claims.

BRIEF DESCRIPTION OF DRAWINGS

FIG. 1 is a simplified flow diagram of a process for butadiene recovery according to embodiments disclosed herein.

As noted, the flow diagrams in FIG. 1 is simplified, and does not illustrate pumps, valves, control valves, filters, reboilers, condensers, and other equipment commonly associated with distillation columns and general petrochemical operations, and these would be understood to be present by one skilled in the art based on the Figures and the Detailed Description provided below.

DETAILED DESCRIPTION

Embodiments disclosed here relate to recovering butadiene from mixed $C_4$ hydrocarbon streams. More specifically, embodiments disclosed herein relate to an improved butadiene extraction process capable of operating at high or low pressure conditions, providing process flexibility.

The $C_4$ fraction to be used as starting mixture in the present processes is a mixture of hydrocarbons having predominantly four carbon atoms per molecule. $C_4$ fractions are obtained, for example, in the preparation of ethylene and/or propylene by thermal or catalytic cracking of a petroleum fraction, such as liquefied petroleum gas, light naphtha or gas oil. $C_4$ fractions may also be obtained by the catalytic dehydrogenation (oxidative and/or non-oxidative dehydrogenation) of n-butane and/or n-butene. The resulting $C_4$ fractions generally include butanes, n-butene, isobutene, 1,3-butadiene and small amounts of $C_3$ and $C_5$ hydrocarbons, including methylacetylene, as well as butynes, in particular 1-butyne (ethylacetylene) and butenyne (vinylacetylene). The 1,3-butadiene content is generally from 5 to 80% by weight. For example, a cracker or a CATADIENE unit may contain 15 to 17% butadiene, by weight. Other mixed $C_4$ feed streams may contain greater or lesser amounts of butadiene. When present in the mixed feed stream, vinylacetylene may be selectively hydrogenated to the desired 1,3-butadiene product prior to feed of the mixed $C_4$ stream to the butadiene extraction unit. In some embodiments, the mixed $C_4$ hydrocarbon stream may be provided, for example, by at least one of cracking, oxidatively dehydrogenating, and non-oxidatively dehydrogenating a $C_4$ hydrocarbon stream comprising butane in one or more dehydrogenation reactors to produce a product gas stream comprising butane, butene, and butadiene.

The above-described hydrocarbon fraction, containing butanes, butenes, 1,2-butadiene, 1,3-butadiene, $C_4$ acetylenes, $C_3$ acetylenes, and $C_{5+}$ hydrocarbons, is fed to a butadiene extraction unit for separation and recovery of the various hydrocarbons, including one or more lights/butanes/butenes fractions (commonly referred to as a Raffinate-1 product), a 1,3-butadiene fraction, a $C_3$ acetylenes (propyne) fraction, a $C_4$ acetylenes fraction, which may include a portion of the 1,2-butadiene, and a heavies fraction, which may include a portion of the 1,2-butadiene and the $C_{5+}$ hydrocarbons. In some embodiments, dimers of butadiene may be formed upstream of the butadiene extraction unit or during processing of the hydrocarbon fraction within the butadiene extraction unit. The vinylcyclohexene components may be recovered with the heavies fraction, or may be recovered as a separate fraction containing vinylcyclohexene.

It has now been found that butadiene extraction processes may be designed for flexible operations, with or without a compressor, while adding little additional capital investment cost. The ability to run at both high and low pressures provides added process flexibility.

Referring now to FIG. 1, a simplified process flow diagram for recovering butadiene at both high and low pressures according to embodiments disclosed herein is illustrated. A mixed hydrocarbon feed 2, including hydrocarbons such as butanes, butenes, 1,2-butadiene, 1,3-butadiene, methyl acetylene, vinyl acetylene, and $C_5+$ hydrocarbons, may be fed to a feed vaporization system 4 to vaporize the mixed hydrocarbon feed. The vaporized feed is then fed via flow line 40 to main wash column 44. In main wash column 44, the vaporized feed is contacted with a solvent fed via flow line 38 and the butanes and butenes are separated from the more soluble 1,3-butadiene, 1,2-butadiene, methyl acetylene, vinyl acetylene, and $C_{5+}$ hydrocarbons.

Solvents useful in the process as illustrated in FIG. 1 may include butyrolactone, nitriles such as acetonitrile, propionitrile, methoxypropionitrile, ketones such as acetone, furfural, N-alkyl-substituted lower aliphatic amides such as dimethylformamide, diethylformamide, dimethylacetamide, diethylacetamide, N-formylmorpholine, N-alkyl-substituted cyclic amides (lactams) such as N-alkylpyrrolidones, especially N-methylpyrrolidone (NMP). In some embodiments, alkyl-substituted lower aliphatic amides or N-alkyl-substituted cyclic amides, dimethylformamide, acetonitrile, furfural or NMP are used.

In some embodiments, it is also possible to use mixtures of these extractants with one another, for example of NMP and acetonitrile, mixtures of these extractants with cosolvents and/or tert-butyl ethers, e.g. methyl tert-butyl ether, ethyl tert-butyl ether, propyl tert-butyl ether, n- or isobutyl tert-butyl ether. In other embodiments, NMP may be in aqueous solution, with from 0 to about 20 weight % water, or with from 7 to 10 weight % water, or with 8 to 8.5 weight % water in other embodiments.

The butanes and butenes are recovered from main wash column 44 as an overheads fraction 8 (Raffinate 1) and a dilution raffinate fraction 9. The enriched solvent, including the dissolved hydrocarbons, is recovered from main wash column 44 as a bottoms fraction 46.

Bottoms fraction 46 is then fed to rectifier 48 to at least partially degas the enriched solvent. Any dissolved butanes and butenes, as well as other light components may be recovered from rectifier 48 as an overheads fraction 50, which may recycled for re-processing in main wash column 44. Methyl acetylene and butadienes, including both 1,2-butadiene and 1,3-butadiene, and $C_{5+}$ hydrocarbons may be recovered from rectifier 48 as overhead draw 52, and a degassed solvent, which may contain various $C_4$ components including 1,2-butadiene, 1-butyne, and vinyl acetylene, may be recovered from rectifier 48 as a bottoms fraction 54.

Bottoms fraction 54 may be fed to a degasser 56, for separation of the solvent, entrained $C_4$ components, and a $C_4$ acetylene fraction, which may also include 1,2-butadiene. The $C_4$ vapors may be recovered from degasser 56 and cooling column 57 as an overheads fraction 58. In some embodiments, operating at conventional low pressures separation conditions, overheads fraction 58 may be compressed via compressor 60; in other embodiments, operating compressorless at high separation pressures, overheads fraction 58 may bypass compressor 60. The desired operating conditions may be effected by opening and closing valves 61A, 61B, 61C to the desired flow path.

The overheads fraction recovered from cooling column 57 may then be recycled, directly without compression or following compression, depending upon the desired operations, to rectifier 48 via flow line 72.

A vinyl acetylene fraction may be withdrawn from degasser 56 as a side draw fraction 62, washed with water fed via line 64 in acetylene washer 66, and recovered as vinyl acetylene fraction 12. Acetylene washer bottoms fraction, recovered via flow line 65, may be recycled back to rectifier 48. A vinyl cyclohexene fraction may be recovered via flow line 13. The degassed solvent may be recovered from degasser 56 as a bottoms fraction 69, for recycle and feed to main wash column 44 and rectifier 48.

The hydrocarbons in overhead draw fraction 52 may be separated from entrained solvent in afterwash column 70. Solvent may be recovered from afterwash column 70 as a bottoms fraction 73 and recycled to rectifier 48, and a crude butadiene product stream may be recovered from afterwash column 70 as an overheads fraction 74.

The crude butadiene product (overheads fraction 74) leaves the extractive distillation section and is then fed to a methyl acetylene distillation column 76, where methyl acetylene is recovered as an overheads fraction 10. The bottoms fraction 78 contains the 1,3-butadiene, 1,2-butadiene, and heavier hydrocarbons, and is fed to butadiene fractionator 80. 1,3-Butadiene having a purity of greater than 99.6% is recovered from butadiene column 80 as an overheads fraction 6, and the 1,2-butadiene and heavies are recovered as a bottoms fraction 14.

In some embodiments, it may be desired to hydrogenate acetylenes in fractions 10, 12 to produce additional olefins and dienes. Additionally or alternatively, it may be desired to use a green oil column to recover oligomers of butadiene (vinyl cyclohexane) and oligomers of other olefinic components in the hydrocarbon feed stream that may be produced during the separations noted above. For example, bottoms fraction 14 may then be combined with feed preheater blowdown stream 51 in drum 53, from which the 1-2 butadiene may be recovered as an overheads draw 55 for eventual combination with vinyl acetylene and recovery via flow stream 12. A heavies fraction, including various C4's, C5's, and heavier compounds may be recovered from drum 53 as a bottoms fraction 63.

To provide efficient operations and minimize capital expenditures to have an option of operating the process with a compressor or without a compressor, such as to save operating costs (electricity, etc.), various aspects of the process must be properly configured or designed. The present process combines the conventional butadiene process with the compressorless process in such a way that both operations are efficient with minimal additional investment cost to the plant to provide the desired flexibility. The aspects used to provide the desired flexibility will now be described in more detail.

As noted above, proper valving must be provided around compressor 60. With valve 61B closed and valves 61A and 61C open, for example, the process may be run in the conventional manner (low pressure). Alternatively, with valves 61A and 61C closed, and valve 61B open, the process may be run compressorless (high pressure).

Due to the differences in operating pressures and temperatures, the various columns, exchangers, and associated piping must be designed to meet requirements over the broader operating window. For example, when running in a high pressure mode (compressorless), degasser 56 may be operated at an overhead pressure of about 4 to about 5 $kg/cm^2$ gage, slightly above the extractive distillation system (including the main washer, rectifier and afterwasher) pressure. Consequently, degasser 56 operates at correspondingly higher temperatures: from about 140° C. to about 160° C. at the top of the degasser and from about 185° C. to about 200° C. at the bottom of the degasser. In contrast, the degasser in the conventional design (low pressure mode) may be operated at an overhead pressure in the range from about 0.5 to about 0.7 $kg/cm^2$ gage, and at much lower temperatures: from about 95° C. to about 115° C. at the top of the degasser and from about 140° C. to about 160° C. at the bottom of the degasser. The higher pressures and temperatures may thus require, for example, minor changes to design parameters for the degasser column (wall thickness, etc.). Heat exchangers associated with degasser 56 (such as reboiler 67, etc.) must also be designed to operate at the different temperatures that may be encountered, where the design must accommodate both temperature and pressure requirements as well as providing sufficient surface area to meet the heat loadings required under the different operating conditions. Heat exchange mediums may also be different for the operations, where medium pressure steam (or sufficient let down from a high pressure steam supply) may be used to provide heat to reboiler 67 during low pressure operations whereas high pressure steam may be required during compressorless operations.

Heat exchange requirements for reboiler 67 is one example of how the overall heat requirements for operation of the two processes, compressorless and traditional, are different, and must be accounted for. Efficient recovery of heat from solvent recirculation must also be designed to accommodate both modes of operation. One possible manner for recovering heat from the solvent circulation loop is illustrated in FIG. 1 (solvent storage not illustrated). During conventional (low pressure) operations, lean solvent recovered from the bottom of degasser 56 via flow line 69 is circulated through valve 30 and first used as a heat exchange medium in reboiler 32 (bottom of the rectifier column 48). The lean solvent may then be used to provide heat in reboiler 34 (bottom of butadiene column 80). The lean solvent may then be used to vaporize a portion of feed 2 in heat exchanger 36. Following recovery of the heat in these exchangers, the lean solvent may then be fed to the top of main wash column 44 and rectifier 48 via flow lines 38 and 39, respectively, for the above-described recovery of butadiene. During compressorless (high pressure) operations, lean solvent recovered from the bottom of degasser 56 via flow line 69 is first used to preheat the degasser feed 54 in exchanger 33, followed by recovery as described above for conventional low pressure operations. Appropriate valving and controls (not illustrated) are included to provide the desired circulation around or through exchanger 33 during low pressure or high pressure operations, respectively.

In both conventional and compressorless operations, heat may also be recovered via a water circulation loop (may contain water and some solvent). For example, water and solvent may be fed via flow line 20 to cooling column 57, and via direct heat exchange recover heat from the degasser 56 overheads fraction 22 and compressor 60 recirculation loop 24. The water/solvent fraction recovered from the bottom of cooling column 57 may then be used to vaporize a portion of feed 2 via indirect heat exchange in exchanger 27 and/or be injected into the bottom of rectifier 48, fed via flow lines 28 ad 29, respectively. Water/solvent exiting heat exchanger 27 may then be recirculated back to cooling column 57 via flow line 20.

In a typical prior art compressorless process, cooling column 57, among other pieces of equipment, is not used, and the solvent heat recovery scheme was changed (re-optimized) to make the process efficient, resulting in changes to many pieces of equipment. As illustrated in FIG. 1, however, the flexible process incorporates the cooling column into the heat recovery system for efficient operation and heat recovery during both conventional and compressorless operations. This greatly minimizes the changes needed to convert from the conventional to the compressorless scheme.

Locations of temperature indicators or thermocouples must also be adapted for both low pressure and high pressure operations. For example, due to the differences in bottoms temperature for degasser column 56, temperature indicator 83 should be appropriately located downstream of bypass line 85. This enables accurate measurement of the temperature of the solvent exiting and/or bypassing exchanger 32, thus allowing for proper control of the amount of solvent fed to exchanger 34 or returned to solvent regeneration (not shown). Similarly, valve trims and other aspects of the numerous pieces of equipment should be properly selected to accommodate the range of flow rates, temperatures, and pressures that may be encountered during both modes of operation.

Flow control may also be adjusted to accommodate both modes of operation. For example, the rate of flow from degasser 56 via side draw 62, measured via flow indicator 91, may be used to control the amount of dilution raffinate fed to the acetylene washer 66 overhead system via flow line 9.

In addition to the above considerations, a digital control system (DCS) or other control means may be configured to control system operations under both operational configurations. For example, during compressorless operations, the amount of lean solvent circulated through exchanger 33 may be controlled to achieve a desired degasser 56 inlet feed temperature. However, when the DCS is switched for low pressure operations, the DCS may disable operations of valves or other components associated with exchanger 33, as it is bypassed. Set points, control parameters (PID settings, etc. for controlling how fast a valve or other equipment reacts to a deviation from set points) and other control aspects may also be configured to automatically change when switching between operational configurations. Additionally, the DCS may be programmed or configured to provide a smooth transition between the operational configurations, such as by ramping up/down compressor operations, exchanger 33 operations, and other aspects of the process to avoid column upsets during the transition period.

As described above, butadiene extraction processes according to embodiments disclosed herein are designed for flexible operations, with or without a compressor, while adding little additional capital investment cost. Previous designs would have required many more changes to the processing scheme, resulting in either more investment cost or a less efficient process. By retaining much of the equipment used in the conventional process, and using this equipment when operating in compressorless mode, butadiene extraction processes according to embodiments disclosed herein are flexible and do not require re-optimization of the solvent heat recovery system. With respect to additional capital expenses, only one additional heat exchanger is required, along with minor changes to controls and equipment design conditions to allow operation at both high and low pressures.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:
1. A system tier recovering 1,3-butadiene from a $C_4$ fraction in both a high pressure mode or a low pressure mode, comprising:
   a feed vaporization system for at least partially vaporizing a hydrocarbon feed containing butanes, butenes, 1,2-butadiene, 1,3-butadiene, $C_4$ acetylenes, $C_3$ acetylenes, and $C_{5+}$ hydrocarbons;
   an extractive distillation system for contacting the vaporized hydrocarbon fraction with a solvent to selectively dissolve a portion of the hydrocarbon fraction forming (a) an enriched solvent fraction comprising the 1,3-butadiene, the 1,2 butadiene, $C_4$ acetylenes, $C_3$ acetylenes, $C_{5+}$ hydrocarbons, and a first portion of the butanes and the butenes and (b) a vapor fraction comprising a second portion of the butanes and the butenes;
   a rectifier and afterwasher for at least partially degassing the enriched solvent and recovering a first vapor fraction comprising the first portion of the butanes and butenes, a second vapor fraction comprising the $C_3$ and $C_4$ acetylenes, 1,3-butadiene, 1,2-butadiene, and $C_{5+}$ hydrocarbons, and a bottoms fraction comprising partially degassed solvent;
   a degasser and cooling column for further degassing the solvent and recovering a liquid fraction comprising degassed solvent, a third vapor fraction comprising at least one of C4 acetylenes and 1,2-butadiene, and a fraction comprising C4 acetylenes;
   wherein the system for recovering 1,3-butadiene is operable for recovering 1,3-butadiene from a $C_4$ fraction (a) with the degasser in a high pressure mode, and (b) with the degasser in a low pressure mode.

2. The system of claim 1, further comprising:
   a compressor for compressing the third vapor fraction when operating in the low pressure mode; and
   a heat exchanger for indirectly heating the partially degassed solvent with the liquid fraction comprising degassed solvent when operating in the high pressure mode.

3. The system of claim 2, wherein valves and flow conduits associated with the heat exchanger and compressor are operable, respectively, such that (a) in low pressure mode, the liquid fraction comprising degassed solvent bypasses the heat exchanger and the third vapor fraction passes through the compressor, and (b) in high pressure mode, the liquid fraction comprising degassed solvent flows through the heat exchanger and the third vapor fraction bypasses the compressor.

4. The system of claim 1, further comprising:
   a control system configured to operate the system for recovering 1,3-butadiene with or without the compressor.

5. The system of claim 4, wherein the control system is further configured to disable or enable operations of portions of the system for recovering 1,3-butadiene based on the selected mode of operation.

6. The system of claim 4, wherein the control system is further configured to transition between the modes of operation.

7. The system of claim 1, wherein the system for recovering 1,3-butadiene is configured such that the cooling column is in operation during both the high pressure mode and the low pressure mode.

8. The system of claim 1, wherein the cooling column, degasser and a degasser reboiler are designed for temperature and pressure conditions required for both modes of operation.

9. A system for recovering 1,3-butadiene from a $C_4$ fraction in both a high pressure mode or a low pressure mode, comprising:
   a feed vaporization system for at least partially vaporizing a hydrocarbon feed containing butanes, butenes, 1,2-butadiene, 1,3-butadiene, $C_4$ acetylenes, $C_3$ acetylenes, and $C_{5+}$ hydrocarbons;
   an extractive distillation system for contacting the vaporized hydrocarbon fraction with a solvent to selectively dissolve a portion of the hydrocarbon fraction forming (a) an enriched solvent fraction comprising the 1,3-butadiene, the 1,2-butadiene, $C_4$ acetylenes, $C_3$ acetylenes, $C_{5+}$ hydrocarbons, and a first portion of the butanes and the butenes and (b) a vapor fraction comprising a second portion of the butanes and the butenes;
   a rectifier and afterwasher for at least partially degassing the enriched solvent and recovering a first vapor fraction comprising the first portion of the butanes and butenes, a second vapor fraction comprising the $C_3$ and $C_4$ acetylenes, 1,3-butadiene, 1,2 butadiene, and $C_{5+}$ hydrocarbons, and a bottoms fraction comprising partially degassed solvent;
   a degasser and cooling column for further degassing the solvent and recovering a liquid fraction comprising degassed solvent, a third vapor fraction comprising at least one of C4 acetylenes and 1,2-butadiene, and a fraction comprising C4 acetylenes;

a compressor for compressing the third vapor fraction when operating in the low pressure mode; and a heat exchanger for indirectly heating the partially degassed solvent with the liquid fraction comprising degassed solvent when operating in the high pressure mode.

10. A system for recovering 1,3-butadiene from a $C_4$ fraction alternatively in a high pressure mode and a low pressure mode, comprising:

a feed vaporization system for at least partially vaporizing a hydrocarbon feed containing butanes, butenes, 1,2-butadiene, 1,3-butadiene, $C_4$ acetylenes, $C_3$ acetylenes, and $C_{5+}$ hydrocarbons;

an extractive distillation system for contacting the vaporized hydrocarbon fraction with a solvent to selectively dissolve a portion of the hydrocarbon fraction forming (a) an enriched solvent fraction comprising the 1,3-butadiene, the 1,2-butadiene, $C_4$ acetylenes, $C_3$ acetylenes, $C_{5+}$ hydrocarbons, and a first portion of the butanes and the butenes and (h) a vapor fraction comprising a second portion of the butanes and the butenes;

a rectifier and afterwasher for at least partially degassing the enriched solvent and recovering a first vapor fraction comprising the first portion of the butanes and butenes a second vapor fraction comprising the $C_3$ and $C_4$ acetylenes, 1,3-butadiene, 1,2-butadiene, and $C_{5+}$ hydrocarbons, and a bottoms fraction comprising partially degassed solvent;

a degasser and cooling column for further degassing the solvent and recovering a liquid fraction comprising degassed solvent, a third vapor fraction comprising at least one of C4 acetylenes and 1,2-butadiene, and a fraction comprising C4 acetylenes;

wherein the system for recovering 1,3-butadiene is configured such that the cooling column is operable during both the high pressure mode and the low pressure mode.

* * * * *